United States Patent [19]

Yoshida et al.

[11] Patent Number: 4,800,085
[45] Date of Patent: Jan. 24, 1989

[54] SLOW-RELEASE COMPOSITE AND PROCESS FOR PRODUCING THE SAME

[75] Inventors: Masaru Yoshida; Masaharu Asano; Isao Kaetsu; Katsuyuki Nakai; Hidetoshi Yamanaka; Keizo Shida, all of Gunma; Akira Shiraishi, Tokyo, all of Japan

[73] Assignees: Japan Atomic Energy Research Institute, Tokyo; Keizo Shida, Gunma; Takeda Chemical Indus. Ltd., Osaka, all of Japan

[21] Appl. No.: 932,874

[22] Filed: Nov. 20, 1986

Related U.S. Application Data

[62] Division of Ser. No. 613,393, May 24, 1984, Pat. No. 4,652,443.

[30] Foreign Application Priority Data

Jun. 7, 1983 [JP] Japan ................................. 58-101319
Jun. 7, 1983 [JP] Japan ................................. 58-101320

[51] Int. Cl.$^4$ ...................... A61K 67/02; A01N 25/26
[52] U.S. Cl. ................................. 424/462; 264/331.14; 514/16; 514/17; 424/468; 424/472
[58] Field of Search .................... 514/16, 17; 424/462, 424/468

[56] References Cited

U.S. PATENT DOCUMENTS 4,659,696  4/1987  Hirai ..................................... 514/16
4,670,419  6/1987  Uda et al. ............................. 514/17

Primary Examiner—Joseph L. Schofer
Assistant Examiner—Peter F. Kulkosky
Attorney, Agent, or Firm—Browdy and Neimark

[57] ABSTRACT

A slow-release composite having pyroglutamyl-histidyl-triptophyl-seryl- tyrosyl-D-leucyl-leucyl-arginyl-proline ethylamide or a salt thereof encapsulated in a polymer matrix and a process the same are herein disclosed.

3 Claims, No Drawings

SLOW-RELEASE COMPOSITE AND PROCESS FOR PRODUCING THE SAME

This is a division of application Ser. No. 613,393 filed May 24, 1984 and now issued as U.S. Pat. No. 4,652,443.

BACKGROUND OF THE INVENTION

The present invention relates to a slow-release composite having encapsulated therein pyroglutamyl-histidyl-triptophyl-seryl-tyrosyl-D-leucyl-leucyl-arginyl-proline ethylamide or a salt thereof, as well as a process for producing the same.

Pyroglutamyl-histidyl-triptophyl-seryl-tyrosyl-D-leucyl-leucyl-arginyl-proline ethylamide or salts thereof (an acetate salt will hereunder sometimes be referred to as TAP-144) were screened during studies on the synthesize LH-RH (luteinizing hormone-releasing hormone) derivatives. This ethylamide has a greater activity than naturally occurring LH-RH and is represented by the following formula:

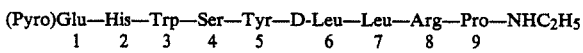

(an abbreviation authorized by IUPAC-IUB Commission on Biological Nomenclature). This compound can be converted to salts by reaction with suitable acids, such as hydrohalogenic acids (e.g. hydrochloric acid and hydrobromic acid), perchloric acid, nitric acid, sulfuric acid, phosphoric acid; and organic acids such as formic acid, acetic acid, propionic acid, lactic acid, pyroracemic acid, oxalic acid, malonic acid, succinic acid, maleic acid, fumaric acid and sulfanic acid. For the sake of convenience, the following description is limited to an acetate salt of the compound, or TAP-144.

When TAP-144 is repeatedly administered to male or female animals, their serum LH and FSH are reduced and the growth of their reproductive organs may sometimes be regulated. In female rats, TAP-144 exhibits the ability to regulate the growth of ovary and control breast cancer induced by 7,12-dimethylbenzene anthracene. Therefore, it is expected that TAP-144 has therapeutic effects on hormone-dependent human breast cancer. In male rats administered TAP-144, there occurs a significant decrease in the weight of the testicles, prostate glands and other secondary reproductive organs, as well as in the amount of serum testosterone. Furthermore, TAP-144 is capable of regulating the growth of tumors transplanted in the prostate glands of a male rat. Therefore, TAP-144 is also expected to have therapeutic effects on human prostatic cancer.

TAP-144 is water-soluble and remains stable in an aqueous solution for at least one year if it is held at room temperature. In order to maximize its pharmacological effects, TAP-144 is daily administered by subcutaneous injection but this may impose an excessive burden on patients.

The present inventors have made various efforts to develop a method of administering TAP-144 by which the pharmacological effects of TAP-144 are retained while imposing minimum burden on patients. As a result, the inventors have found that this object can be achieved by using a slow-release formulation wherein TAP-144 is encapsulated in a polymer matrix. The present invention has been accomplished on the basis of this finding.

SUMMARY OF THE INVENTION

One object of the present invention is to provide a slow-release composite having TAP-144 encapsulated therein, and a process for producing the same.

Another object of the present invention is to provide a slow-release composite having at least one shaped element of TAP-144 which is encapsulated in a vinyl monomer or polyethylene fluoride matrix.

Still another object of the present invention is to provide a process for producing a slow-release composite comprising the step of shaping TAP-144 into a suitable form under pressure, surrounding at least one shaped element of TAP-144 with one or more polymerizable vinyl monomers, polymerizing said vinyl monomers by illumination with light or ionizing radiation at low temperatures so as to produce a vinyl polymer in which the TAP-144 is encapsulated.

A further object of the present invention is to provide a process for producing a slow-release composite comprising the step of shaping TAP-144 into a suitable form under pressure, placing at least one shaped element of TAP-144 in position, placing a filler between two shaped elements of the TAP-144 and/or on either top or bottom or both of the shaped element, surrounding the shaped TAP-144 element (or elements) with one or more polymerizable vinyl monomers, polymerizing said vinyl monomers by illumination with light or ionizing radiation at low temperatures so as to produce a vinyl polymer in which is encapsulated the TAP-144 as sandwiched between two layers of the filler.

A still further object of the present invention is to provide a slow-release composite, which comprises the step of encapsulating TAP-144 in polyethylene fluoride which optionally contains a porous material and which is capable of being shaped to a membrane by compression, and subsequently compressing the combination of TAP-144 and polyethylene fluoride to the desired shape at a pressure between 50 and 1,000 kg/cm$^2$.

These and other objects and advantages of the present invention will become apparent by reading the following description taken in conjunction with the accompanying drawings.

BRIEF DESCRIPTION OF THE DRAWINGS

FIGS. 1 to 7 show the profiles of in vitro release of TAP-144 from the composites of the present invention that were prepared in Examples 1 to 22.

DETAILED DESCRIPTION OF THE PREFERRED EMBODIMENTS

The slow-release composite of the present invention having encapsulated therein pyroglutamyl-histidyl-triptophyl-seryl-tyrosyl-D-leucyl-leucyl-arginyl-proline ethylamide or a salt thereof can be produced by the following method: (1) forming the active compound or a salt thereof into a suitable shape by compression; (2) placing at least one shape element in position, optionally with a filler of a suitable shape being positioned between two shaped elements and/or on either top or bottom or both of the shaped element; (3) surrounding the assembly with at least one polymerizable monomer which will not crystallize at low temperatures and instead provide easily a stable supercooled or glassy structure, or with a mixture of such a monomer and at least one polymerizable monomer which does not form by itself a supercooled or glassy structure at low temperatures but which will form, with the aid of the first type of monomer, a polymer at low temperatures; (4) polymerizing the first monomer, optionally together with the second monomer, by illumination with light or ionizing radiation at a temperature ranging from room temperature to −200° C.

In the first step of the process described above, TAP-144 is shaped to a suitable form at a pressure which is properly selected from the range of 100 to 1,000 kg/cm$^2$, usually from the range of 100 to 600 kg/cm$^2$, depending upon the shape to be obtained. TAP-144 may be shaped to a tablet, membrane, particle, disk, needle, cube or any six-sided solid form depending upon the manner of the intended use of the slow-release composite. The slow-release composite of the present invention may be embedded in a diseased site of the patient by a surgical method or may be directly applied to the site with a syringe or any other suitable means.

In the second step, at least one shaped element of TAP-144 is placed in a suitable container. If more than one shaped element of TAP-144 is used, the respective elements are stacked one on top of another with a suitable clearance being left between each element. In the third step, one or more polymerizable vinyl monomers are charged into the container so as to surround completely the one or more shaped elements of TAP-144 in the container. If only one shaped element of TAP-144 is used, it may be sandwiched by a layer of filler. If more than one shaped element of TAP-144 is used, a filler may be disposed on both sides of each TAP-144 and between two TAP-144 elements. This arrangement permits the active compound to be released from the final composite at a controlled rate.

It is important for the purposes of the present invention that the slow-release composite be prepared in such a manner that TAP-144 is initially released at low rate. The present inventors have found that this requirement can be met by one of the following techniques.

(A) If one face of the shaped TAP-144 is positioned closer to the bottom of the composite, a thicker layer of polymer is formed above the TAP-144, and it takes a lnger time for the TAP-144 to be released from the upper part of the composite. Therefore, the release rate of TAP-144 is governed by its release from the bottom portion of the composite. With this type of the composite, the release rate of TAP-144 can be controlled to some extent by selecting a proper substrate in which to encapsulate the TAP-144.

(B) If the shaped TAP-144 is positioned in close contact with both sides of the polymer, the TAP-144 release rate is governed by the release from the top and bottom of the composite.

(C) By placing a filler on both sides of the shaped TAP-144 or by putting a filler between two shaped TAP-144 elements, the distance between the surfaces of the polymer and shaped TAP-144 can be controlled in such a manner that the initial release of TAP-144 from the composite is held low.

As shown above, the initial TAP-144 release from the composite can be controlled by physical means such as proper selection of the position of shaped TAP-144 in the composite or the use of a filler. The initial release rate of TAP-144 can be varied over a wide range by controlling the hydrophilicity, porosity and adsorbability of the polymer.

The amount of TAP-144 to be encapsulated in the composite of the present invention should be properly determined by the use and shape of the composite. The TAP-144 is practically immiscible with most high-molecular weight substances and, furthermore, it is labile and decomposed to lose its activity at elevated temperatures. Therefore, one feature of the present invention is that a monomer polymerizable at low temperatures is selected as a substrate in which to encapsulate TAP-144. It is well known that an advantageous method of polymerization at low temperatures is to use light or ionizing radiation because it requires an extremely small activation energy for initiating the polymerization reaction. However, ordinary polymerizable monomers easily crystallize at low temperatures, and because of the limited movement of monomer molecules and the extremely low growth reaction rate, these monomers either become unpolymeriazble or achieve only a very small polymerization rate. Therefore, a method which performs polymerization at low temperatures by simply cooling a polymerizable monomer is unable to satisfy the two conflicting requirements, i.e. high polymerization rate and controlled polymerization temperature.

As a result of various studies made to perform polymerization at low temperatures and to increase the polymerization rate while controlling the polymerization temperature, the present inventors have found that these objects can be attained by using a glass-forming monomer. Having a special molecular structure, this monomer will not crystallize at low temperatures and easily form a stable supercooled or glassy structure without losing the polymerizability. Polymerization of a glass-forming monomer in the supercooled state could be described as a solid phase polymerization in the non-crystalline state, and because of its high polymerizing ability in the low temperature range, this method is most effective for fixing, or making a slow-release agent from a physiologically active substance which by nature is easily deactivated with heat. Examples of the glass-forming polymerizable monomer that can be used in the present invention include ethylene dimethacrylate, diethylene glycol dimethacrylate, diethylene glycol diacrylate, triethylene glycol dimethacrylate, triethylene glycol diacrylate, tetraethylene glycol dimethacrylate, tetraethylene glycol diacrylate, polyethylene glycol dimethacrylate, polyethylene glycol diacrylate, diethylaminoethyl dimethacrylate, glycidyl methacrylate, epoxy acrylate, glycidyl acrylate, hydroxyethyl methacrylate, hydroxyethyl acrylate, hydroxypropyl methacrylate, hydroxypropyl acrylate, hydroxybutyl methacrylate, hydroxybutyl acrylate, hydroxyhexyl methacrylate, hydroxyhexyl acrylate, butanediol dimethacrylate, butanediol diacrylate, propanediol dimethacrylate, propanediol diacrylate, pentanediol dimethacrylate, pentanediol diacrylate, hexanediol dimethacrylate, hexanediol diacrylate, neopentyl glycol dimethacrylate, neopentyl glycol diacrylate, trimethylolpropane triacrylate, trimethylolpropane trimethacrylate, trimethylolethane triacrylate, trimethylolethane trimethacrylate, polypropyleneglycol diacrylate, and polypropylene glycol dimethacrylate. And a polymerizable monomer selected from the group consisting of diethylene glycol dimethacrylate, polyethylene glycol dimethacrylate, 2-hydroxyethyl methacrylate, trimethylpropane trimethacrylate, neopenthyl glycol dimethacrylate, methoxypolyethylene glycol methacrylate and combination thereof is preferably used. And, a polymerizable monomer selected from the group consisting of diethylene glycol dimethacrylate, polyethylene glycol #600 dimethacylate, 2-hydroxyethyl methacrylate and a combination thereof is most preferably used.

In addition to the glass-forming polymerizable monomers listed above, the present invention permits the use of one or more polymerizable monomers which are unable to produce a supercooled or glassy structure by themselves but which, when mixed with the glass-forming monomer in specific proportions, are capable of polymerization at low temperatures. Examples of this second type of monomers include acrylic acid, methacrylic acid, vinylpyrrolidone, acrylamide, methacrylamide, vinyl acetate, vinyl propionate, styrene, vinyltoluene, divinylbenzene, methyl methacrylate, ethyl methacrylate, propyl methacrylate, butyl methacrylate, pentyl methacrylate, hexyl methacrylate, octyl methacrylate, lauryl methacrylate, benzyl methacrylate, cyclohexyl methacrylate, stearyl methacrylate, methyl acrylate, butyl acrylate, ethyl acrylate and maleic anhydride. These monomers may be used in an amount not exceeding 40% of the total weight of the first and second monomers used.

The proportions of TAP-144 and polymerizable monomers used in the practice of the present invention should be properly determined by the size of the desired composite, its shape, intended use and the properties it is required to have. As a guide figure, a tablet of TAP-144 weighing 100 mg and having a diameter of 11 mm and a thickness of 0.5–0.7 mm may be used in combination with 0.5 to 1.0 cc of the polymerizable monomers.

According to the present invention, a crystallizable component may be used together with the polymerizable monomers for the purpose of controlling the release rate of TAP-144 from the composite. Suitable examples of such crystallizable component include water, dioxane, ethylene glycol, polyethylene glycol, cyclohexane, benzene, acetic acid, propionic acid, butyric acid, urea, crotonic acid, maleic acid, malic acid, succinic acid, sorbic acid, itaconic acid, n-decane, n-nonane, n-hexane, n-heptane, paraffin, stearic acid, palmitic acid, lauryl alcohol, octyl alcohol, caprylic acid, caproic acid, capric acid, stearyl alcohol, palmityl alcohol, butyl stearate, methyl stearate, methyl acetate, ethyl acetate, butyl acetate, propyl acetate and propionamide.

The compressed TAP-144 encapsulated in one or more of the polymerizable monomers listed above is subsequently illuminated with light or ionizing radiation in the temperature range of room temperature to $-200°$ C. so as to polymerize the monomers and produce a slow-release composite having TAP-144 encapsulated in the polymer matrix. Various light sources can be used for initiating the polvmerization, and they include visible UV rays from low- or high-pressure mercury lamp; sunlight; light, X-rays, gamma-rays, bata-rays, electron beam and alpha-rays from photon factories; mixed radiation from chemonuclear reactors; and gamma-rays from spent fuels or fission products. With the use of ionizing radiation, the dose rate generally ranges from $1 \times 10^4$ to $1 \times 10^9$ R/hr to give a total dose which usually ranges from $1 \times 10^4$ to $5 \times 10^6$ R, preferably from $1 \times 10^5$ to $1 \times 10^6$ R.

As already mentioned, a suitable filler may be used with the shape TAP-144 for the purpose of controlling the initial release of TAP-144 from the composite. If one shaped element of TAP-144 is encapsulated in the polymer matrix, the filler may be positioned on at least one side of the TAP-144. If two or more shaped elements of TAP-144 are to be encapsulated in the polymer matrix, the filler may be positioned between each TAP-144 element and/or on both sides of the TAP-144 element. These embodiments are also included in the scope of the present invention. A suitable filler is selected from among those substances which can be incorporated in the living body for an extended period without causing any deleterious effects. Exemplary fillers include biodegradable polymers such as gelatin, thermally denatured protein, polylactide and polyamino acids, as well as conventional synthetic polymers, glass fibers, paraffin, filter paper and natural fibers. These fillers are used in the form of woven or nonwoven fabrics, membranes and filaments.

While one aspect of the present invention wherein TAP-144 is encapsulated in a vinyl polymer matrix has been described above, the invention has another aspect wherein TAP-144 is encapsulated in polyethylene fluoride, as shown below.

According to this second aspect, TAP-144 is first encapsulated in polyethylene fluoride which can be shaped into a membranous form by compression and which may contain a porous material as required. Then, the assembly is shaped by compression at between 50 and 1,000 kg/cm$^2$ to provide the desired slow-release composite.

TAP-144 can be encapsulated in polyethylene fluoride by one of the following two techniques. In one method, a layer of polyethylene fluoride is placed on the bottom of a forming vessel made of a suitable pressure-resistant material such as metal. Then, TAP-144 is uniformly dispersed on the polyethylene fluoride layer, and this uniform dispersion of TAP-144 is covered with another layer of polyethylene fluoride. In the second method, TAP-144 is compressed into a suitable shape before it is encapsulated in the polyethylene fluoride. The shaping of TAP-144 may be effected at a pressure in the range of 50 to 1,000 kg/cm$^2$, and a suitable pressure is usually selected from the range of 100 to 600 kg/cm$^2$ depending upon the desired shape of TAP-144, which may be a tablet, membrane, particle, disk, needle, cube or any six-sided solid depending upon the specific manner of the use of the slow-release composite. If the composite is to be embedded in the skin, the TAP-144 is preferably in the form of a disk with a flat bottom. At least one shaped element of TAP-144 is encapsulated in polyethylene fluoride in a forming vessel as in the first method. If a plurality of shaped elements of TAP-144 are to be encapsulated, they are stacked one on top of another with a suitable distance provided between each element.

Polyethylene fluoride used as a substrate for encapsulating TAP-144 is prepared by polymering an ethylene monomer wherein at least one hydrogen atom of the ethylene is substituted by a fluorine atom. This polymer is highly resistant to heat and chemicals, and at the same time, it has a high degree of biocompatibility because of its inertness in the living body. The type and the method of synthesis of the polyethylene fluoride are not critical so long as it can be shaped into a membranous form by compression at room temperature. Typical examples of the polyethylene fluoride that can be used in the present invention include polytetrafluoroethylene resins 5-J, 7-J, 7A-J, 30-J, 6-J, 6C-J and 62-J, all of which are available from Mitsui Fluorochemicals Co., Ltd., as well as Teflon 120 which is a copolymer of ethylene fluoride and propylene. The thickness of the polyethylene fluoride layer in which to encapsulate the compressed TAP-144 should be properly determined by the intended use of the composite and the desired release rate of TAP-144 from the composite. If a fast release rate is needed, a thin layer of polyethylene fluoride is used, and if a slow rate is desired, a thick layer of polyethylene fluoride is selected.

Polyethylene fluoride is hydrophobic, so a membrane shaped from it repels water and retards the release of TAP-144 from the composite. Some uses of the composite require the TAP-144 to be released at a controlled rate. In such cases, a porous material may be incorporated in the polyethylene fluoride before its shaping. Porous materials that can be used for this purpose include silica gel, activated carbon, molecular sieve and gelatin.

Polyethylene fluoride in which TAP-144 has been encapsulated in the forming vessel is subsequently compressed to the desired shape at between 50 and 1,000 kg/cm$^2$. The higher the pressure that is applied, the greater the strength of the membrane that is obtained, and this tends to decrease the release rate of TAP-144 from the composite. Therefore, the pressure used to shape the polyethylene fluoride should be properly selected depending upon the intended use of the composite. The shaping of the polyethylene fluoride is typically effected at or around room temperature.

The composite thus prepared which has TAP-144 encapsulated in the polyethylene fluoride matrix may be buried in an affected site of the patient by a surgical technique or may be directly applied to the site with a syringe or any other suitable means. In any event, the best method of use should be determined depending upon the severity of the tumor and its site.

The features and advantages of the present invention are hereunder described in greater detail by reference to the following illustrative working examples, wherein in vitro tests for the release of TAP-144 from the composite were conducted at 37° C. using a 0.1M phosphate buffer solution (pH 7.4) as a release medium.

EXAMPLES 1 AND 2

Two flat-bottom disks (dia. 11 mm) of TAP-144 (200 mg) were prepared by compression at 400 kg/cm$^2$. Each disk was placed in the center of the bottom of a flat-bottom glass ampule (I.D. 15 mm). One ampule was charged with 0.4 ml of a polymerizable monomer mixture consisting of 80% diethylene glycol dimethacrylate and 20% polyethylene glycol (#600) dimethacrylate (Example 1). The other ampule was charged with 1.0 ml of the same monomer mixture (Example 2). After fusing at 10$^{-3}$ mmHg, the ampules were cooled to −78° C. with a dry ice-ethanol coolant and subsequently irradiated with gamma-rays from cobalt-60 for 2 hours at a dose rate of 5×10$^5$ rad/hr so as to polymerize the monomers. The resulting two slow-release composites were subjected to an in vitro TAP-144 release test, the results of which are shown in FIG. 1. The curve —o—o— indicates the release profile of the composite prepared in Example 1 and the curve         the profile of the composite prepared in Example 2.

EXAMPLES 3 AND 4

Two slow-release composites were prepared by repeating the procedure of Example 1 except that the polymerizable monomer mixture was replaced by 0.4 ml of 2-hydroxyethyl methacrylate (Example 3) and by 0.4 ml of trimethylolpropane trimethacrylate. The release profiles of TAP-144 from the composites are shown in FIG. 2 (Example 3) and FIG. 3 (Example 4).

EXAMPLE 5

A slow-release composite was prepared as in Example 2 except that five flat-bottom disks (dia. 11 mm) of TAP-144 were encapsulated in the polymer matrix. The profile of TAP-144 release from the composite is shown in FIG. 4.

EXAMPLE 6

TAP-144 (300 mg) was shaped into a disk (dia. 11 mm) with a flat bottom at a pressure of 500 kg/cm$^2$. The disk was placed in a glass ampule (I.D. 16 mm), with a glass fiber mat (dia. 11 mm, thickness: 1 mm) being placed on both sides of the TAP-144 disk. The ampule was then charged with 0.6 ml of a polymerizable monomer mixture consisting of 70% neopentyl glycol dimethacrylate and 30% methoxypolyethylene glycol (#1000) methacrylate, which was polymerized as in Example 1 to prepare a filler containing composite. The profile of TAP-144 release from the composite is shown in FIG. 5.

EXAMPLES 7 TO 10

Slow-release composites were prepared as in Example 6 except that the glass fiber mat was replaced by the following fillers: a human gamma-globulin film prepared by heat treatment at 90° C. for 4 seconds at a pressure of 100 kg/cm$^2$ (Example 7), a gelatin film (Example 8), gause specified in the Japanese Pharmacopoeia (Example 9) and paraffin paper (Example 10). The profiles of TAP-144 release from the respective composite are shown in FIG. 5, in which the curves —o—o—, — □- □-, △—△—, ●—● —and—■ -■— respectively indicate the release profiles of the composites prepared in Examples 6 to 10.

EXAMPLE 11

TAP-144 (1 g) was shaped into a square membrane (4 cm×4 cm) by compression at 600 kg/cm$^2$. This membrane was placed in a glass vessel, with a patch (4 cm×4 cm×0.1 mm) of EPTEF® of Japan Geretex Co., Ltd. being placed as a filler on both sides of the TAP-144 membrane. The glass vessel was charged with a polymerizable monomer mixture consisting of 50% glycidyl acrylate and 50% hydroxyethyl acrylate. The amount of the monomer mixture was so determined that it would provide a composite having a thickness of 5 mm. After closing the vessel, the contents were solidified at −24° C. with a mixture of carbon tetrachloride and liquid nitrogen. In an atmosphere of nitrogen gas, the solidified contents were irradiated with gamma-ryas from cobalt-60 for 4 hours at a dose rate of 5×10$^5$ rad/hr. As a result, a slow-release composite in the form of a higly flexible membrane was obtained, in which TAP-144 was encapsulated in the polymer matrix. The profile of TAP-144 release from the composite is shown in FIG. 6.

EXAMPLES 12 AND 13

Two flat-bottom disks (dia. 11 mm) of TAP-144 (200 mg) were prepared by compression at 400 kg/cm$^2$. Each disk was placed in the center of the bottom of a flat-bottom glass ampule (I.D. 15 mm). One ampule was charge with 0.4 ml of a polymerizable monomer mixture consisting of 80% diethylene glycol dimethacrylate and 20% polyethylene glycol (#600) dimethacrylate (Example 12). The other ampule was charged with 1.0 ml of the same monomer mixture (Example 13). After fusing at $10^{-3}$ mmHg, the ampules were rapidly cooled to $-30°$ C., and subsequently illuminated with a high-pressure mercury lamp for 120 minutes so as to polymerize the monomers. The resulting two slow-release composites were subjected to an in vitro TAP-144 release test, the results of which were very similar to those obtained with the composites prepared in Examples 1 and 2.

EXAMPLES 14 TO 16

Three flat-bottom disks (dia. 11 mm) of TAP-144 (500 mg) were prepared by compression at 500 kg/cm$^2$. Teflon 7A-J (350 mg) of Mitsui Fluorochemicals Co., Ltd. was placed on the bottom of three metallic vessels (I.D. 15 mm), and overlaid with each of the TAP-144 disks, which was further covered with 350 mg of Teflon 7A-J. The three combinations of TAP-144 and Teflon 7A-J were compressed at room temperature at 100 kg/cm$^2$ (Example 14), 300 kg/cm$^2$ (Example 15) and 600 kg/cm$^2$ (Example 16). Each of the resulting composites was rigid and had TAP-144 sandwiched between two Teflon 7A-J layers.

The composites were subjected to an in vitro TAP-144 release test, the results of which are shown in FIG. 7. The curves A to C respectively indicate the profiles of TAP-144 release from the composites prepared in Examples 14 to 16.

EXAMPLES 17 TO 19

Three slow-release composites were prepared as in Example 16 except that Teflon 7A-J was replaced by Teflon 6C-J of Mitsui Fluorochemicals Co., Ltd. (Example 17), Teflon 5-J of Mitsui Fluorochemicals Co., Ltd. (Example 18) and Teflon 120 (Example 19).

The results of an in vitro TAP-144 release test conducted with the composites are shown in FIG. 7, wherein the curves D, E and F indicate respectively the release profiles for the composites prepared in Examples 17, 18 and 19.

EXAMPLE 20

TAP-144 (300 mg) was shaped into a flat-bottom disk (dia. 10 mm) by compression at 400 kg/cm$^2$. The disk was placed in a metallic vessel (I.D. 16 mm) and encapsulated in Teflon 7A-J (400 mg) containing silica gel (100–300 mesh). The assembly was compressed at 200 kg/cm$^2$ to obtain a slow-release composite in the form of a flat-bottom disk (dia. 6 mm).

EXAMPLES 21 AND 22

Slow-release composites in the form of a flat-bottom disk (dia. 16 mm) were prepared as in Example 20 except that the silica gel was replaced by 50 mg of activated carbon of 400–500 mesh (Example 21) and by 50 mg of gelatin of 100–200 mesh (Example 22).

The three slow-release composites were subjected to an in vitro TAP-144 release test, and the average of the respective release profiles is indicated by curve G in FIG. 7.

What is claimed is:

1. A slow-release composite consisting essentially of a core of pyroglutamyl-histidyl-triptophyl-seryl-tyrosyl-D-leucyl-leucyl-arginyl-proline ethylamide or a salt thereof, as active ingredient, encapsulated in a membranous form of polyethylene fluoride, which is produced by:
   compressing said active ingredient into a shaped body; and
   encapsulating said shaped body with said polyethylene fluoride.

2. A slow-release composite according to claim 1 wherein the salt is an acetic acid salt.

3. The product of claim 1 formed by compressing said active ingredient into said shaped body at 50–1000 kg/cm$^2$.

* * * * *